(12) United States Patent  (10) Patent No.: US 8,430,988 B2
Patterson et al.  (45) Date of Patent: Apr. 30, 2013

(54) REINFORCED MULTI-LUMEN CATHETER

(75) Inventors: Ryan C. Patterson, Farmington, UT (US); Walter H. Shang, Irvine, CA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 13/088,156

(22) Filed: Apr. 15, 2011

(65) Prior Publication Data

US 2011/0192008 A1    Aug. 11, 2011

Related U.S. Application Data

(62) Division of application No. 12/698,999, filed on Feb. 2, 2010, now Pat. No. 7,972,465, which is a division of application No. 11/025,319, filed on Dec. 29, 2004, now abandoned.

(60) Provisional application No. 60/533,683, filed on Dec. 31, 2003.

(51) Int. Cl.
*B29C 65/00* (2006.01)
*B32B 37/00* (2006.01)
*C08J 5/00* (2006.01)
*A61M 25/00* (2006.01)

(52) U.S. Cl.
USPC ....... 156/304.6; 156/86; 156/296; 156/304.2; 156/308.2; 604/284; 604/526

(58) Field of Classification Search .......... 156/84, 156/86, 184, 185, 187, 188, 190, 191, 192, 156/195, 242, 243, 244.11, 244.13, 244.15, 156/244.18, 244.19, 244.24, 244.25, 244.27, 156/250, 254, 296, 297, 304.1, 304.2, 304.3, 156/304.6, 308.2, 309.6, 323; 604/264, 284, 604/523, 525, 526, 527

See application file for complete search history.

(56) References Cited

U.S. PATENT DOCUMENTS

| | | |
|---|---|---|
| 2,211,975 A | 8/1940 | Hendrickson |
| 2,458,305 A | 1/1949 | Sanders |
| 3,416,531 A | 12/1968 | Edwards |
| 3,489,626 A | 1/1970 | Rubenstein |
| 3,598,126 A | 8/1971 | Hoeltzenbein |

(Continued)

FOREIGN PATENT DOCUMENTS

| | | |
|---|---|---|
| EP | 1699517 A2 | 9/2006 |
| WO | 9942156 A1 | 8/1999 |
| WO | 2005065761 A2 | 7/2005 |
| WO | 2011123818 A1 | 10/2011 |

OTHER PUBLICATIONS

EP 04815836.4 filed Dec. 29, 2004 Office Action dated Jan. 23, 2008.

(Continued)

*Primary Examiner* — Philip Tucker
*Assistant Examiner* — Brian R Slawski
(74) *Attorney, Agent, or Firm* — Rutan & Tucker LLP

(57) ABSTRACT

A reinforced multi-lumen catheter and method of manufacturing the same. An assembly for manufacturing the multi-lumen catheter includes a proximal catheter body substrate including a septum, a first and second distal catheter body substrate, a first and second mandrel, a reinforcing element and a sleeve. The reinforcing element is positioned over the proximal catheter body substrate and at least a proximal region of the first and second distal catheter body substrates.

10 Claims, 6 Drawing Sheets

U.S. PATENT DOCUMENTS

| | | |
|---|---|---|
| 3,684,605 A | 8/1972 | Zwart |
| 4,044,765 A | 8/1977 | Kline |
| 4,256,146 A | 3/1981 | Genini et al. |
| 4,516,972 A | 5/1985 | Samson |
| 4,581,012 A | 4/1986 | Brown et al. |
| 4,619,643 A | 10/1986 | Bai |
| 4,634,432 A | 1/1987 | Kocak |
| 4,804,359 A | 2/1989 | Grunwald et al. |
| 4,840,622 A | 6/1989 | Hardy |
| 4,961,809 A | 10/1990 | Martin et al. |
| 5,041,083 A | 8/1991 | Tsuchida et al. |
| 5,063,018 A | 11/1991 | Fontirroche et al. |
| 5,087,246 A | 2/1992 | Smith |
| 5,190,520 A | 3/1993 | Fenton, Jr. et al. |
| 5,221,255 A | 6/1993 | Mahurkar et al. |
| 5,269,752 A | 12/1993 | Bennett |
| 5,279,596 A | 1/1994 | Castaneda et al. |
| 5,334,167 A | 8/1994 | Cocanower |
| 5,370,685 A | 12/1994 | Stevens |
| 5,378,230 A | 1/1995 | Mahurkar |
| 5,380,276 A | 1/1995 | Miller et al. |
| 5,405,338 A | 4/1995 | Kranys |
| 5,441,489 A | 8/1995 | Utsumi et al. |
| 5,454,795 A | 10/1995 | Samson |
| 5,460,608 A | 10/1995 | Lodin et al. |
| 5,476,453 A | 12/1995 | Mehta |
| 5,486,159 A | 1/1996 | Mahurkar |
| 5,571,093 A | 11/1996 | Cruz et al. |
| 5,584,803 A | 12/1996 | Stevens et al. |
| 5,603,705 A | 2/1997 | Berg |
| 5,613,980 A | 3/1997 | Chauhan |
| 5,674,208 A | 10/1997 | Berg et al. |
| 5,676,659 A | 10/1997 | McGurk |
| 5,685,841 A | 11/1997 | Mackool |
| 5,695,483 A | 12/1997 | Samson |
| 5,766,151 A | 6/1998 | Valley et al. |
| 5,830,196 A | 11/1998 | Hicks |
| 5,858,009 A | 1/1999 | Jonkman |
| 5,863,366 A | 1/1999 | Snow |
| 5,876,386 A | 3/1999 | Samson |
| 5,879,499 A | 3/1999 | Corvi |
| 5,899,891 A | 5/1999 | Racz |
| 5,902,282 A | 5/1999 | Balbierz |
| 5,911,715 A | 6/1999 | Berg et al. |
| 5,945,052 A | 8/1999 | Schryver et al. |
| 5,947,953 A | 9/1999 | Ash et al. |
| 5,951,495 A | 9/1999 | Berg et al. |
| 5,954,651 A | 9/1999 | Berg et al. |
| 6,001,079 A | 12/1999 | Pourchez |
| 6,004,310 A | 12/1999 | Bardsley et al. |
| 6,019,778 A | 2/2000 | Wilson et al. |
| 6,024,693 A | 2/2000 | Schock et al. |
| 6,036,682 A | 3/2000 | Lange et al. |
| 6,045,734 A | 4/2000 | Luther et al. |
| 6,103,037 A * | 8/2000 | Wilson .......................... 156/158 |
| 6,152,912 A | 11/2000 | Jansen et al. |
| 6,190,349 B1 | 2/2001 | Ash et al. |
| 6,212,422 B1 | 4/2001 | Berg et al. |
| 6,258,080 B1 | 7/2001 | Samson |
| 6,273,876 B1 | 8/2001 | Klima et al. |
| 6,280,423 B1 | 8/2001 | Davey et al. |
| 6,332,892 B1 | 12/2001 | Desmond, III et al. |
| 6,394,141 B2 | 5/2002 | Wages et al. |
| 6,425,898 B1 | 7/2002 | Wilson et al. |
| 6,447,488 B2 | 9/2002 | Estabrook et al. |
| 6,464,684 B1 | 10/2002 | Galdonik |
| 6,482,171 B1 * | 11/2002 | Corvi et al. ................. 604/96.01 |
| 6,482,211 B1 | 11/2002 | Choi |
| 6,503,353 B1 * | 1/2003 | Peterson et al. ................. 156/86 |
| 6,505,066 B2 | 1/2003 | Berg et al. |
| 6,508,804 B2 | 1/2003 | Sarge et al. |
| 6,585,705 B1 | 7/2003 | Maginot et al. |
| 6,595,966 B2 | 7/2003 | Davey et al. |
| 6,659,134 B2 | 12/2003 | Navis |
| 6,695,832 B2 | 2/2004 | Schon et al. |
| 6,702,782 B2 | 3/2004 | Miller et al. |
| 6,702,972 B1 * | 3/2004 | Markle ......................... 264/230 |
| 6,709,429 B1 | 3/2004 | Schaefer et al. |
| 6,719,749 B1 | 4/2004 | Schweikert et al. |
| 6,758,836 B2 | 7/2004 | Zawacki |
| 6,872,198 B1 | 3/2005 | Wilson et al. |
| 6,881,211 B2 | 4/2005 | Schweikert et al. |
| 7,018,374 B2 | 3/2006 | Schon et al. |
| 7,393,339 B2 | 7/2008 | Zawacki et al. |
| 7,972,465 B2 | 7/2011 | Patterson et al. |
| 2001/0001814 A1 | 5/2001 | Estabrook et al. |
| 2001/0016730 A1 | 8/2001 | Martins et al. |
| 2001/0021840 A1 | 9/2001 | Suresh et al. |
| 2002/0190453 A1 * | 12/2002 | Wilhelm et al. ............... 267/248 |
| 2003/0097091 A1 | 5/2003 | Hobbs et al. |
| 2003/0105427 A1 * | 6/2003 | Lee et al. ................. 604/103.04 |
| 2003/0153898 A1 * | 8/2003 | Schon et al. ................... 604/544 |
| 2004/0039369 A1 | 2/2004 | Shelso |
| 2004/0089969 A1 | 5/2004 | Willard |
| 2004/0167463 A1 | 8/2004 | Zawacki et al. |
| 2004/0210187 A1 | 10/2004 | Zawacki |
| 2005/0054990 A1 | 3/2005 | Graft et al. |
| 2005/0131356 A1 | 6/2005 | Ash et al. |
| 2005/0182387 A1 | 8/2005 | Webler |
| 2005/0209572 A1 | 9/2005 | Rome et al. |
| 2005/0209584 A1 | 9/2005 | Rome |
| 2006/0015086 A1 | 1/2006 | Rasmussen et al. |
| 2006/0020256 A1 | 1/2006 | Bell et al. |
| 2007/0005003 A1 | 1/2007 | Patterson et al. |
| 2009/0182361 A1 | 7/2009 | Thompson et al. |
| 2010/0082000 A1 | 4/2010 | Honeck et al. |
| 2010/0132879 A1 | 6/2010 | Patterson et al. |
| 2011/0245806 A1 | 10/2011 | Patterson |

OTHER PUBLICATIONS

Neocork Technologies, Synthetic Premium Co-Extruded Corks, <<http:www.neocork.com/co_extrusion.html>>, last accessed Mar. 10, 2011, ©2010.

PCT/US2004/043840 filed Dec. 29, 2004 International Preliminary Report on Patentability dated Jul. 3, 2006.

PCT/US2004/043840 filed Dec. 29, 2004 Search Report dated Jul. 28, 2005.

PCT/US2004/043840 filed Dec. 29, 2004 Written Opinion dated Jul. 28, 2005.

PCT/US2011/030997 filed Apr. 1, 2011 International Search Report and Written Opinion dated Jun. 14, 2011.

U.S. Appl. No. 11/025,319, filed Dec. 29, 2004 Final Office Action dated Jun. 1, 2009.

U.S. Appl. No. 11/025,319, filed Dec. 29, 2004 Non-Final Office Action dated Jul. 7, 2008.

U.S. Appl. No. 11/025,319, filed Dec. 29, 2004 Non-Final Office Action dated Nov. 20, 2008.

U.S. Appl. No. 12/698,999, filed Feb. 2, 2010 Notice of Allowance dated Jan. 24, 2011.

* cited by examiner

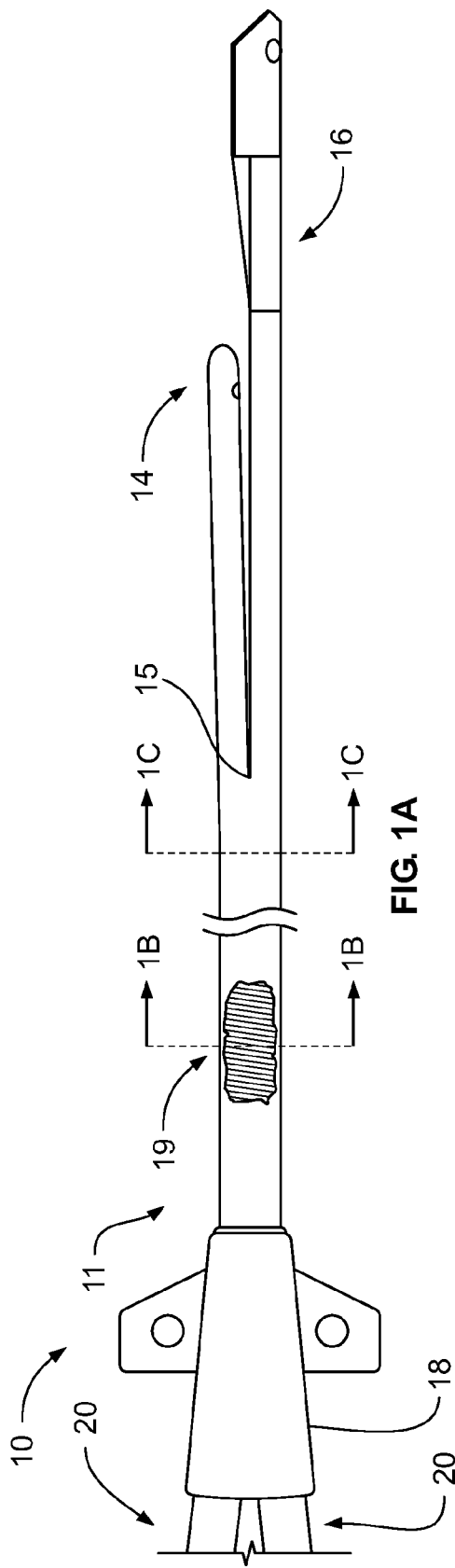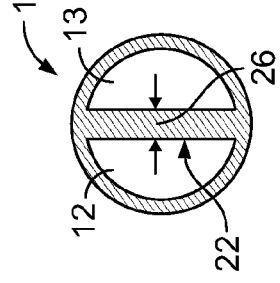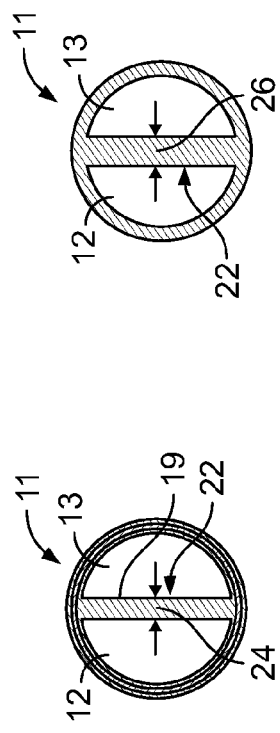

REINFORCED MULTI-LUMEN CATHETER

CROSS-REFERENCE TO RELATED APPLICATIONS

This application is a division of U.S. patent application Ser. No. 12/698,999, filed Feb. 2, 2010, now U.S. Pat. No. 7,972,465 which is a division of U.S. patent application Ser. No. 11/025,319, filed Dec. 29, 2004, now abandoned, which claims the benefit of U.S. Provisional Application No. 60/533,683, filed Dec. 31, 2003, each of which is expressly incorporated by reference as if fully set forth herein.

BACKGROUND OF THE INVENTION

Multi-lumen catheters are used for the purpose of creating two or more separate fluid pathways, such as in hemodialysis applications. A primary goal of hemodialysis access is to provide a reliable and effective means of dialysis, which means that a sufficient volume of blood over a period of time must be removed from and returned to the patient. Because the contaminated and cleansed blood must be kept separate for an effective dialysis procedure, a dual lumen catheter is generally used. Typically, a dual lumen catheter for hemodialysis is configured so that there is a shorter lumen that aspirates blood from a blood vessel of a patient to a dialysis machine where it is processed for the removal of toxins, and a longer lumen that infuses the purified blood to the patient. The shorter lumen utilized for aspiration is generally referred to as the "arterial lumen," while the longer lumen utilized for infusion is generally referred to as the "venous lumen." The reason for the different lengths is to minimize co-mingling of aspirated and infused blood.

The primary problems occurring in dual lumen dialysis catheters include thrombosis and fibrin sheath formation, which can act to occlude distal tips of the dialysis catheter lumens, resulting in loss of catheter function when such an occlusion prevents blood flow. This typically occurs initially in the arterial lumen used for aspiration of blood from a patient. A secondary problem relates to the arterial lumen "sucking" against the vessel wall, in which the arterial lumen openings become fully occluded by the patient's vasculature. To specifically address these problems, a unique type of dialysis access catheter has been designed that utilizes independent "free floating" distal tip sections that separate at a distal end of the catheter in order to reduce the likelihood of potential occlusion and "sucking" during dialysis treatment, hereinafter referred to as a "split-tip catheter." Examples of patents and patent applications describing split-tip catheters include U.S. Pat. No. 6,001,079 to Pourchez, U.S. Pat. No. 6,758,836 to Zawacki, U.S. Pat. No. 7,393,339 to Zawacki, and co-pending U.S. patent application Ser. No. 10/842,586, filed May 10, 2004, all of which are incorporated by reference herein.

While the split-tip catheter design has led to improved functioning of dialysis catheters, it has been difficult to manufacture a split-tip catheter having reinforcement along a length thereof due to the change in configuration at the distal end. As one of skill in the art readily appreciates, a reinforcing region is desirable in an implanted catheter to prevent kinking of the catheter and/or a reduction in the catheter lumen(s) due to external pressures. Accordingly, provided herein are improvements to the design and manufacture of a multi-lumen catheter, and in particular a split-tip catheter, with respect to reinforcement along a length thereof.

BRIEF SUMMARY OF THE INVENTION

In accordance with the invention described herein, several embodiments are disclosed, which may be improvements to prior art split-tip catheters or may be novel catheter embodiments heretofore undisclosed. As used herein, the following terms have the following meanings:

"Reinforcing region" refers to the region or section of the catheter body which has been reinforced with a reinforcing element.

"Reinforcing element" refers to a material or materials that provide kink-resistance, columnar strength, etc. to the reinforcing region and includes, but is not limited to, a wire or wires, a coil or coils, braiding, or other reinforcement means. This term is not intended as limiting and should not be construed as such, for example, with respect to particular material(s), shapes, sizes, thicknesses, lengths and/or disposition thereof with respect to the catheter body.

"Septum" refers to a dividing element within a catheter body that defines separate lumens therein. The septum may be integrally formed with the catheter body or may be formed separately to be inserted within a lumen of the catheter body.

"Split-tip catheter" refers to a catheter having a body enclosing at least two lumens and a dividing point that separates at least two tip sections from one another distal thereto, each of the tip sections enclosing at least one lumen and being separated or separable from one another along their length.

"Dividing point" refers to a point along the length of the split-tip catheter distal to which at least two tip sections are separated or are separable from one another.

"Tip section" refers to a portion of the split-tip catheter, enclosing at least one lumen, which is separable or is separated from another tip section along its length distal to a dividing point.

In one embodiment, a multi-lumen catheter is provided with a septum having a cross-sectional thickness in a distal region that is greater than a cross-sectional thickness in a proximal region. The difference in septum thickness is provided to enhance functionability particular to the proximal and distal end of the catheter. Thus, the proximal region of the catheter will generally be constructed with a relatively thin septum to allow for better overall flow performance, while the distal region of the catheter will generally be constructed with a relatively thick septum to allow the catheter to be split and tipped in a secondary production procedure, which provides numerous manufacturing advantages. In particular, the septum distal region may be cut using a razor or other tool once the catheter has been constructed. In order to impart additional kink resistance and support to the septum proximal region, a reinforcing region may be provided over the outer wall of the catheter along at least a portion of the length of the septum proximal region. One noted advantage to such a design is that a catheter can be provided with different lumen cross-sectional areas along the length of the catheter without altering the catheter outer diameter, thereby minimizing the risk of air embolism during placement of the catheter through an introducer sheath when compared with a catheter in which the outer diameter varies along with the variation of lumen cross-sectional area.

A shrink down method can be utilized to produce the above-described embodiment. In one manufacturing variation, two D-shaped mandrels are placed within D-shaped lumens of a dual lumen catheter substrate (e.g., a tube having an outer wall enclosing a centrally positioned septum that defines two lumens having approximately the same size and shape). The cross-sectional shapes of the mandrels may be different at a proximal end and a distal end. For example, the distal end of at least one of the mandrels may be stepped or tapered such that the cross-sectional area of the distal end is less than that of the proximal end, thereby allowing for the formation of a thicker septum at the distal end of the catheter for reasons discussed above. A reinforcing element is then positioned over at least a proximal portion of the substrate and a sleeve is placed over the entire assembly. Shrink tubing is placed over the sleeve and heat is applied, causing the shrink tubing to compress the reinforcing element onto the underlying substrate, which in turn causes the inner lumens to conform to the mandrel shapes. Because the lumens tend to conform to the shape of the mandrels during this process, extra material may be added to a distal portion of the substrate over the stepped or tapered portion of the mandrels to ensure that the final outer diameter of the catheter remains constant. The extra material can be provided, for example, by an additional sleeve over the distal section of the substrate and/or by thin strips of polyurethane inserted into voids between the mandrels and septum wall in the lumens of the distal section where the mandrels extend. After heating, the shrink tubing is removed and a tipping process is performed. In one variation, the lumens are separated at the distal end of the catheter, for example, by cutting through the septum.

In another manufacturing variation of the present invention, the reinforced multi-lumen catheter is constructed utilizing two dual lumen substrates, including a proximal substrate having a relatively thin septum and a distal substrate having a relatively thick septum. Two D-shaped mandrels are placed through the lumens of the proximal substrate and into the proximal end of the distal substrate. The proximal and distal substrates are brought into contact with one another and a reinforcing element is disposed over the proximal substrate (and may overlap onto the distal substrate to fortify the bond between the proximal and distal substrates). A sleeve is then placed over the entire assembly and shrink tubing is placed over the sleeve. Heat is applied, causing the sleeve to melt onto the substrates and causing the inner lumens to conform to the mandrel shapes. The shrink tubing is then removed and the distal end of the catheter undergoes a tipping procedure.

In yet another manufacturing variation of the present invention, a reinforced split-tip catheter can be constructed utilizing a proximal dual lumen substrate and two separate D-shaped lumen substrates. Two D-shaped mandrels are placed through the lumens of the proximal substrate and into the proximal end of the distal substrates. The proximal and distal substrates are brought into contact with one another and a reinforcing element is disposed over the proximal substrate (and may overlap onto the distal substrate to fortify the bond between the proximal and distal substrates). A sleeve is then placed over the assembly, extending to a point proximal the distal end of the D-shaped lumen substrates and shrink tubing is placed over the sleeve. Heat is applied, causing the sleeve to melt onto the substrates and causing the inner lumens to conform to the mandrel shapes. The shrink tubing is then removed. The separate D-shaped lumen substrates should already be separated over their length distal to where the sleeve and shrink tubing extended and thus, further separation tipping procedures are not necessary. However, refinement of the tips and/or other finishing processing is possible.

It should be noted that the tensile strength of the bond between thick and thin septum sections may be improved by moving the bond to a location beneath the reinforcing element, meaning that the transition from thin to thick septum portion occurs within the reinforcing region in the above-described variations. This improved bond strength may be particularly useful in the case where two D-shaped lumen substrates are bonded onto a proximal dual lumen substrate.

In another embodiment of the present invention, a multi-lumen catheter is created by inserting an independently formed septum into a catheter body. The independently formed septum may exhibit varying longitudinal geometric and material properties to affect local properties along the length of the catheter assembly (i.e., bending stiffness, kink resistance, varying lumen area, etc.). For example, the septum could have a thicker distal end to facilitate tipping, as discussed above, or could be pre-split at a distal end thereof for the manufacture of a split-tip catheter. Other variations include altering the cross-sectional geometry of the septum to optimize flow.

In one manufacturing variation of the present invention, an independently formed septum is inserted into a lumen of a cylindrical tube that has been provided with a reinforcing element. There are various ways to assure that the septum and the tube fit tightly together prior to bonding. In one variation, a longitudinal strain can be applied to the septum during insertion in order to temporarily reduce the cross sectional area of the septum. Once the septum is in position within a lumen of the outer tube, the tension is released, allowing the septum to expand. The reinforcing element prevents the cylindrical tube from being deformed into an oval cross-sectional shape when the septum is allowed to expand. In another variation, the inner surface of the outer tube is modified (e.g., a notch or recessed area is provided) to accommodate the septum so that insertion thereof is facilitated without affecting the cross-sectional shape of the cylindrical tube. The septum is bonded to the cylindrical tube by chemical (e.g., solvent bonding), ultrasonic, heat-shrink, or other methods known to one of skill in the art.

In another manufacturing variation of the present invention, a first cylindrical tube is extruded and an independently formed septum is placed in the lumen of the first tube along with accompanying mandrels (e.g., a pair of D-shaped mandrels are placed on either side of a septum having a rectangular cross-sectional shape such that the cross-section of the septum and mandrels form a circle filling the lumen of the tube). A reinforcing element is then positioned over the assembly, followed by a second cylindrical tube. Shrink tubing is placed over the second cylindrical tube and heat is applied, melting the component parts together, encapsulating the reinforcing element between the first and second tubes and bonding the septum to the first tube. Thereafter, the mandrels are removed and further tipping procedures are performed as necessary.

In yet another manufacturing variation of the present invention, an independently formed septum and shaped mandrels are combined to form a core assembly (e.g., a pair of D-shaped mandrels are placed on either side of a septum having a rectangular cross-sectional shape such that the cross-section of the septum and mandrels form a circle filling the lumen of the tube). A coated reinforcing element is then wrapped around the core assembly and shrink tubing is placed thereover. Heat is then applied, compressing and heating the coated reinforcing element to melt the component parts together, after which the mandrels are removed and further tipping procedures are performed as necessary. Certainly, as is the case with all described embodiments herein, numerous variations are possible with respect to the physical properties (e.g., shape, size, material, etc.) of both the septum and mandrel(s).

In another embodiment of the present invention, a multi-lumen catheter is created using two thin-walled D-shaped lumen substrates and two D-shaped mandrels that are placed within each substrate such that the mandrels fit snugly therein. The substrates are then assembled together to form a circle in cross-section (i.e., the flat sides of each are adjoining) and a reinforcing element is positioned over the assembled substrates over a proximal portion thereof (i.e., a distal portion is left uncovered by the reinforcing element). A sleeve is placed over the entire assembly and a shim is inserted between the lumens at the distal end thereof (e.g., extending approximately 7-8 cm). Utilizing shrink tubing and heat, the assembly is then melted together, after which the mandrels and shrink tubing are removed. The result is a final product having an proximal outer diameter greater than a distal outer diameter. In one variation, instead of a single sleeve being placed over the assembly, two sleeves are employed, wherein a distal sleeve has a greater wall thickness than a proximal sleeve in order to produce a final product with substantially the same outer diameter. The sleeve portion that surrounds the channel formed by the shim is then slit, resulting in a split-tip distal section. The shim itself may have sharp edges to accomplish the slitting process. The shim can be made of metal (e.g., stainless steel), PTFE or other material with sufficient tensile strength and smoothness to enable the removal thereof following the heating process.

In one variation, the D-shaped lumen substrates are formed to have a thicker septum than wall (i.e., the flat side of the D-shaped substrate is thicker than the round side thereof). In another variation, a single D-shaped substrate is formed and is cut along its length to provide two D-shaped substrates. The lengths of the two substrates could be approximately the same or one could be longer than the other. In another variation, the mandrels placed within the lumens of the substrates could be shaped with a slight bow on the side that contacts the flat portion of the substrates to produce a septum that is slightly thicker at the top and bottom thereof, which results in a catheter better adapted for high negative pressure in that the arterial lumen is more resistant to deformation and collapse. During the assembling process, a fixture apparatus may be used to both hold the mandrels in place to avoid relative movement and to rotate the mandrels for disposition of the reinforcing element. Moreover, the manufacturing process may include a "pre-shrink" process in which hot air is blown over the assembly while the assembly is rotated. Further, the heating step herein may include the use of a convection oven, in which the temperature is set at the melt temperature of the sleeve or sleeves and the assembly is heated for a time sufficient to permit the material to flow.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 1A is a perspective view of a split-tip catheter made according to the present invention.

FIG. 1B is a cross-sectional view of the split-tip catheter of FIG. 1A taken along line "B-B."

FIG. 1C is a cross-sectional view of the split-tip catheter of FIG. 1A taken along line "C-C."

DETAILED DESCRIPTION OF THE INVENTION

Figure 2:
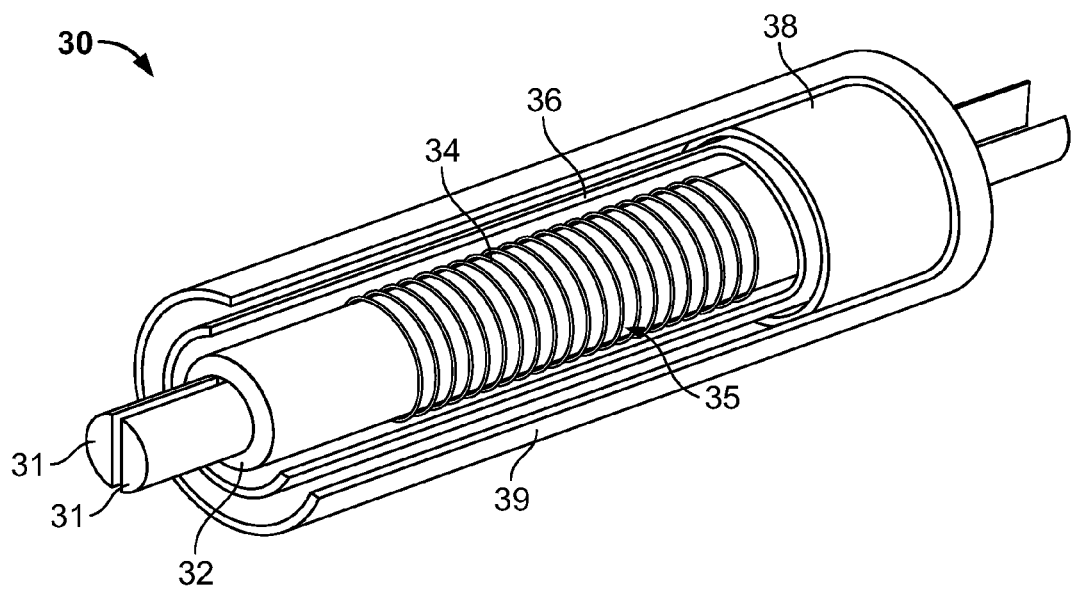
FIG. 2 is a cut-away view of an assembly for the manufacture of a multi-lumen catheter according to the present invention, showing the component parts through the outer wall of the sleeve.

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

It should be appreciated that while many of the designs and methods for making a multi-lumen catheter discussed herein are particular to a split-tip catheter, they would be equally applicable to other types of catheters. Therefore, the examples and embodiments provided herein should not act to limit the scope of the present invention to split-tip catheters. Further, while examples are provided herein with respect to materials for component parts of the described multi-lumen catheter, the invention should not be limited to these materials as numerous other materials not specifically mentioned herein, which are well-known to one of skill in the art, are equally contemplated for use in construction of the inventive catheter.

In addition, the description of the manufacture of a multi-lumen catheter herein focusses on the catheter body which comprises that region of a multi-lumen catheter distal to an extracorporeal connector (e.g., Y-connector, etc.) utilized to fluidly connect the catheter lumens to one or more devices outside of the body. Although not specifically described herein, the present invention is intended to encompass all types of connectors utilized in conjunction with multi-lumen catheters and therefore should not be limited to specific connectors or connector systems for use therewith. For example, while not specifically discussed herein, the multi-lumen catheter of the present invention could be formed with an integral connector at the proximal end thereof or could be constructed to accommodate an attachable/detachable connector, as described, for example, in commonly assigned co-pending U.S. patent application Ser. Nos. 10/803,207 and 10/803,512, filed Mar. 18, 2004, each of which are incorporated by reference herein.

FIG. 1A is a perspective view of an example of a multi-lumen catheter made according to the present invention.

Split-tip catheter 10 has catheter body 11 enclosing two lumens 12, 13 (FIGS. 1B and 1C) that are defined by an outer wall and a bisecting planar septum 22 of the catheter body 11. The two lumens 12, 13 extend from the proximal end of the catheter to the distal end thereof and have a D-shape configuration due to the planar septum 22. The proximal end of the catheter is attached to a Y-connector 18, which in turn is connected to extension tubing 20, as is standard in dialysis catheters. The Y-connector 18 and extension tubing 20 fluidly connect the lumens to a blood treatment unit or dialysis machine (not shown). The distal end of the split-tip catheter 10 is bifurcated into a pair of distal tip sections 14, 16, which are distal to a dividing point 15. Each of the tip sections 14, 16 enclose a lumen that is respectively continued from the pair of distinct lumens 12, 13 enclosed in the catheter body 11. The catheter body also includes a reinforcing element 19 along a length thereof, extending from a proximal portion to a distal portion, but terminating proximal the dividing point 15. The septum 22 of split-tip catheter 10 has a cross-sectional thickness that is greater along a distal region than along a proximal region as shown in FIGS. 1B and 1C. In particular, septum cross-sectional thickness 26 along a distal region is greater than septum cross-sectional thickness 24 along a proximal region.

In one variation for manufacturing a multi-lumen catheter of the present invention, a shrink down method is utilized, wherein the component parts of the catheter are assembled, shrink tubing is positioned over the component parts and the entire assembly is heated to melt the component parts together. The primary component parts utilized for the manufacture of a multi-lumen catheter of the present invention include, but are not limited to: one or more mandrels, one or more catheter body substrates, a septum within the one or more catheter body substrates that is either integrally formed with the substrate(s) or is a separately formed component to be inserted therein, a reinforcing element and one or more sleeves. Of course, depending on the particular embodiment, there are numerous other possible component parts, some of which will be discussed in detail below. Also, while not specifically discussed herein, one or more adhesive layers can be utilized to assist in the bonding of the component parts.

Examples of materials used for the catheter body substrates, septum and sleeves of the present invention include, but are not limited to, medical grade polyurethane including Carbothane® (e.g., Barium filled 85 Shore A), silicone, polyvinylchloride (PVC) and polytetrafluoroethylene (PTFE). Examples of materials used for the shrink tubing include fluorinated ethylene propylene (FEP), PTFE and ethylenetetrafluoroethylene (ETFE). In one example, the mandrels are made of stainless steel and have a Teflon® coating disposed thereon to facilitate insertion and withdrawal into and out of the lumens of the catheter body substrate(s). The reinforcing element can comprise a wire, ribbon, etc. that is either braided or helically wrapped directly onto the catheter body substrate or that is first encased or surrounded by a polymer or other type of material along its length. Examples of possible materials for the reinforcing element include, but are not limited to, stainless steel, Nitinol, polytetrafluoroethylene (PTFE), high density polyethylene (HDPE) and high durometer polyurethanes.

Figure 3:
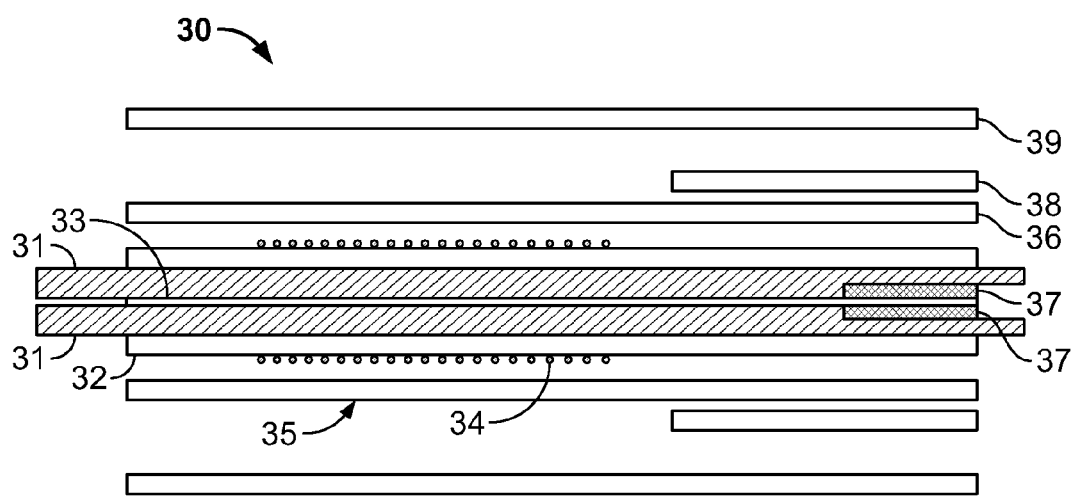
FIG. 3 is a cross-sectional exploded view of the assembly of FIG. 2.

A cut-away view of an assembly of one variation of the present invention is illustrated in FIG. 2. Assembly 30 includes two D-shaped mandrels 31, a catheter body substrate 32, a reinforcing element 34 disposed over a proximal region of the catheter body substrate 32, a first sleeve 36 positioned over the catheter body substrate 32 and reinforcing element 34, a second sleeve 38 positioned over a distal portion of the catheter body substrate 32, and shrink tubing 39 positioned over the sleeve 38. FIG. 3 illustrates the assembly 30 of FIG. 2 in a lengthwise cross-sectional view. From this view, strips of material 37 can be seen, which in this example are utilized to produce a thicker distal septum. In assembly 30, two D-shaped mandrels 31 are inserted within a dual lumen substrate 32 such that each mandrel extends beyond both proximal and distal ends thereof as shown in FIGS. 2-3. The mandrels 31 are sized to conform to the desired lumen geometry of the substrate 32 and, in one variation, are sized slightly smaller in cross-section than the lumens of the substrate so that they can easily be inserted therethrough. The substrate 32 may be formed through extrusion, injection molding or other processes known to one of skill in the art with an integral septum 33 dividing the substrate into substantially equivalent portions. The substrate 32 may have many cross-sectional shapes, but in this example is circular. Likewise, although a septum could be placed in various different locations within the substrate 32 and itself may have numerous different cross-sectional shapes and sizes to create two or more lumens of varying configurations, the septum 33 in this example has a rectangular cross-section and is positioned within the substrate 32 to create similarly-sized D-shaped lumens.

As mentioned, a thicker septum at the distal end of a multi-lumen catheter according to the present invention provides certain advantages in facilitating tipping procedures following initial formation of the catheter body. For example, if a split-tip catheter is being produced, having a thicker distal septum eases the step of cutting the septum to create distal tip sections. Thus, as shown in FIG. 3, the mandrels 31 have a step at the distal end thereof, which when placed within the lumens of the substrate 32 create a void between the mandrels 31 and the septum 33. Of course, the same effect can be achieved through a distal taper of the mandrels as well. The thicker septum is created at the distal end upon heating whereby material flows into the voids. However, in order to ensure that the outer diameter of the catheter body remains substantially the same before and after heating, additional material may be positioned at the distal end of the assembly 30, including, for example, strips of material 37, a distal sleeve 38 or both. Of course, it may also be possible to create the catheter body substrate with a septum that increases in thickness from a proximal to distal end, in which case it may not be necessary to utilize the distal sleeve 38 and/or the strips of material 37.

Following the insertion of the mandrels 31 into the lumens of the catheter body substrate 32, the reinforcing element 34 is positioned around the outer wall of the substrate 32, creating a reinforcing region 35. The reinforcing region 35 may extend from a proximal region of the catheter to a distal region thereof (making certain that the reinforcing region 35 does not extend past the desired location of the dividing point). In the variation shown in FIGS. 2-3, the reinforcing element 34 extends at least to the point along the length of the catheter body substrate where the septum 33 increases in thickness so that the catheter body region with a thinner relative septum is provided with additional support. A sleeve 36 is positioned over the reinforcing element 34 and the remainder of the catheter body substrate 32 and a distal sleeve 38 is then optionally positioned over a distal region of the sleeve 36. In one variation, the sleeve 36 is sized slightly larger than the outside diameter of the substrate 32 to facilitate positioning (e.g., 0.020 in. larger diameter) and similarly, the distal sleeve 38 is sized slightly larger than the sleeve 36. Optionally, as mentioned above, strips of material 37 may also be positioned within the lumens of the catheter substrate 32 at the distal end thereof between the septum 33 and the mandrels 31.

Shrink tubing 39, which in one variation is sized to easily slide over sleeves 36, 38, is positioned over sleeve 36 and sleeve 38. The assembly 30 is then heated to a temperature suitable to compress the shrink tubing 39 onto the sleeves 36, 38, such that the reinforcing element is encapsulated between the outer wall of the catheter body substrate 32 and the sleeve 36, the lumens of the catheter body substrate 32 conform to the shapes of the mandrels, and the component parts of the assembly 30, including the strips 37, melt together to form a final catheter body. In one variation, FEP is utilized for the shrink tubing 39 and the assembly 30 is heated, for example in a convection oven, to a temperature of between approximately 300° C. and 360° C. for a time of between approximately 1 and 5 minutes. Following formation of the catheter body, the assembly 30 is permitted to cool at room temperature and the shrink tubing 39 is removed. Tipping procedures are then implemented, which include, but are not limited to: cutting the distal septum in a proximal direction to a predetermined point, resulting in the formation of a dividing point and two distal tip sections, using tipping procedures known in the art to configure the tips to a desired geometry (e.g., using radio-frequency energy to round the tips) and forming side holes in the distal tip sections. Also, as discussed above, the catheter body can undergo additional manufacturing steps with respect to configuring the proximal end of the catheter to accommodate an attachable connector or connector system.

Figure 4:
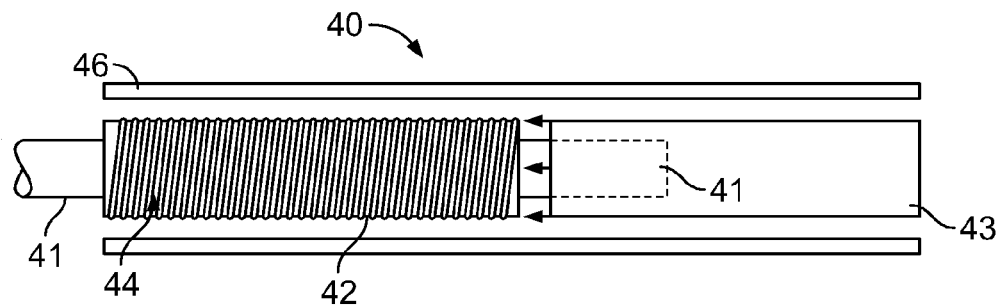
FIG. 4 is a cross-sectional view of another embodiment of an assembly for the manufacture of a multi-lumen catheter according to the present invention.

In one variation of the present invention, instead of a single catheter body substrate, two catheter body substrates are utilized to form the multi-lumen catheter as shown in FIG. 4. Assembly 40 includes a proximal catheter body substrate 42 having a septum with a first thickness and a distal catheter body substrate 43 having a septum with a second thickness, wherein the second thickness is greater than the first thickness. Although in this example, the catheter body substrates 42, 43 have lumens that are approximately equivalent in size and shape, it should be appreciated that the shapes and sizes of the respective lumens of catheter body substrates 42, 43 can be manipulated through the use of mandrels along with elevated temperatures as the lumens will conform to the shape of the mandrels. In this example, the mandrels 41 have D-shaped cross-sections to match the D-shaped lumens of the catheter body substrates 42, 43; however, any shape and size of mandrel may be utilized to impart a desired geometry to the catheter lumens. Although certainly contemplated as one possibility, the mandrels 41 in this example do not extend through the entire length of the catheter body substrates 42, 43 and instead extend through the proximal body substrate 42 and into only a proximal region of the distal catheter substrate 43.

Once the mandrels 41 have been inserted, the proximal and distal catheter body substrates 42, 43 are brought into abutting relationship with one another and the reinforcing element 44 is positioned around the outer wall of at least a portion of the proximal catheter body substrate in order to provide rigidity due to the relative thinness of the septum thereof. In addition, the reinforcing element 44 may be positioned over at least the proximal end of the distal catheter body substrate 43 to improve the tensile strength of the bond between substrates 42, 43. In one variation, the reinforcing element 44 is positioned around a majority of the length of the proximal catheter body substrate 42 as well as a proximal region of the distal catheter body substrate 43. A sleeve 46 is then placed over the substrates 42, 43 and the reinforcing element 44, followed by shrink tubing, which is positioned over the sleeve 46. Heat is then applied to the assembly as discussed above and the shrink tubing is removed for further tipping procedures, if necessary.

Figure 5:
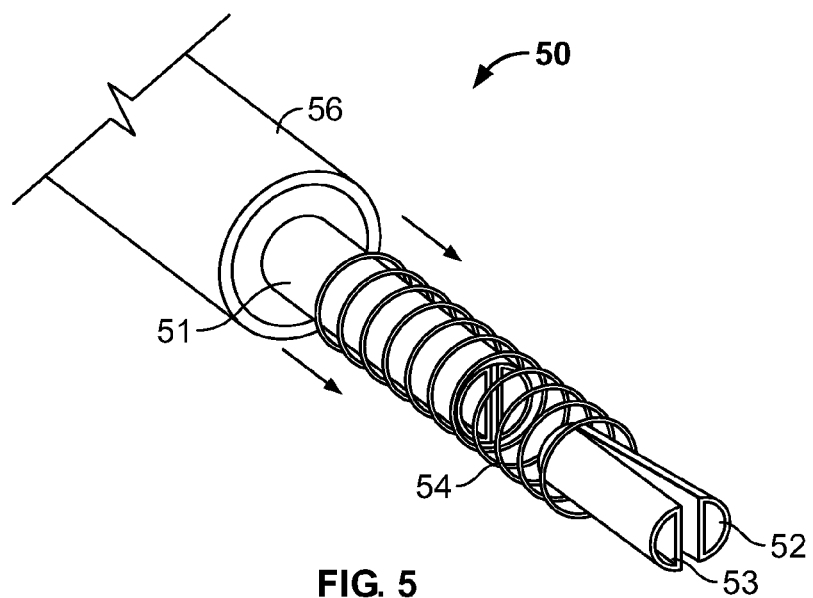
FIG. 5 is a perspective view of one variation of an assembly for the manufacture of a multi-lumen catheter according to the present invention.

In another variation, of the present invention, three catheter body substrates are utilized, as illustrated in FIG. 5. Assembly 50 comprises a proximal catheter body substrate 51 and two distal catheter body substrates 52 and 53. In this example, the proximal catheter body substrate 51 has a dual lumen configuration with two D-shaped lumens separated by a septum, while each distal catheter body substrate 52, 53 has a single D-shaped lumen and has a semi-circular cross-sectional shape. In one variation, the distal catheter body substrates 52 and 53 have different lengths. For example, in a hemodialysis application, distal catheter body substrate 52 can be longer than distal catheter body substrate 53, such that when implanted in a patient, substrate 53 is utilized for aspiration of blood, while substrate 52 is utilized for infusion of blood, in order to minimize co-mingling of aspirated and infused blood. Providing substrates 52, 53 having final desired lengths with respect to one another simplifies the tipping procedures necessary following assembly of the catheter. As with the previous examples, mandrels are inserted through the proximal catheter body substrate 51 and into either just a proximal end of the distal catheter body substrates 52, 53 or completely therethrough. The substrates 51, 52, 53 are then brought into abutting relationship with one another and a reinforcing element 54 is disposed about the proximal catheter body substrate 51 and optionally over a proximal region of the distal catheter body substrates 52, 53 in order to fortify the bond between the substrates. A sleeve 56 is then positioned over the proximal catheter body substrate 51 and at least a proximal region of the distal catheter body substrates 52, 53 and shrink tubing is positioned over the sleeve. The entire assembly 50 is heated and the shrink tubing is removed for further tipping procedures, if necessary.

Figure 6:
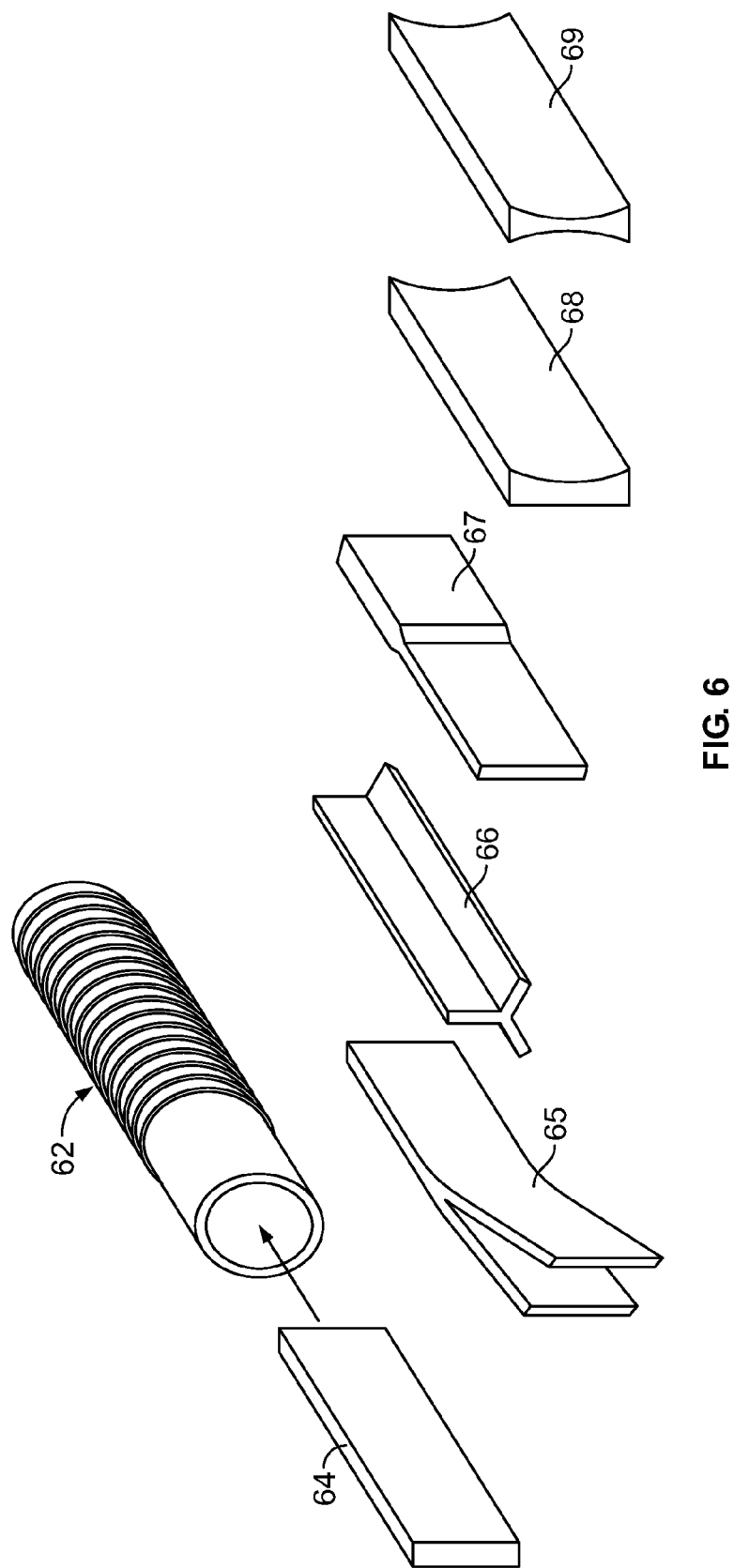
FIG. 6 is a view of component parts of another embodiment of an assembly for the manufacture of a multi-lumen catheter according to the present invention, showing several possibilities for the independent septum portion.

In another embodiment of the present invention, a multi-lumen catheter is created using an independently formed septum, which is inserted into a reinforced substrate. The reinforced substrate is produced by first providing a tubular substrate, which in one variation has a thin wall (e.g., a thickness of between approximately 0.003 in. and 0.020 in.), and positioning the substrate over a mandrel, such as a high density polyethylene (HDPE) mandrel. A reinforcing element is then disposed about the tubular substrate and adhered thereto by either embedding the reinforcing element in the wall of the substrate, utilizing an adhesive, positioning a sleeve over the reinforcing element and heating (as described above), or by other methods known to one of skill in the art. Next, as illustrated in FIG. 6, the mandrel is removed and a preformed septum 64 is inserted into the lumen of the reinforced substrate 62. After insertion, the septum 64 is bonded to the substrate 62 by known methods, such as solvent bonding, ultrasonic bonding, heat shrink bonding, etc.

While the septum 64 has a uniform rectangular shape, there are numerous other possibilities for the septum shape, some of which are also illustrated in FIG. 6, including pre-split septum 65, triple lumen septum 66, varying thickness septum 67, single arched septum 68 and double arched septum 69. Some of the advantages to the varying thickness septum 67 are described above, whereas one advantage of the arched septum 68 and double arched septum 69 is that it imparts optimal flow to a catheter in that the arched shape defining a catheter lumen is more resistant to lumen closure when withdrawing blood or fluid therethrough. Depending on the type of catheter to be formed, the septum can take on any desired shape and size. Because the septum is inserted following manufacture of a reinforced substrate, a multi-lumen catheter may be produced with thinner walls and thus a smaller outside diameter due to the elimination of the necessity of providing wide tolerances. With particular respect to providing pre-split septum 65, manufacture of a split-tip catheter is facilitated in that tipping procedures involving the slicing or cutting of the septum (as described above) are unnecessary. With respect to the triple lumen septum 66, the varying thickness septum 67, the arched septum 68, the double arched septum 69 and other preformed septum designs, including pre-split septum 65, manufacture of a catheter incorporating the preformed septum is facilitated due to ease of forming a thin-walled tube as opposed to a catheter with a complex lumen configuration, as well as, in some variations, the elimination of the use of D-shaped mandrels in the bonding process. Further, the outside diameter of a multi-lumen catheter formed by this method can be more tightly controlled.

Figure 7A:
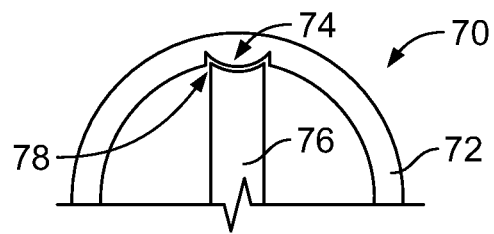
FIG. 7A is a cross-sectional view of a portion of a catheter substrate and a septum in one variation of the embodiment of FIG. 6.
Figure 7B:
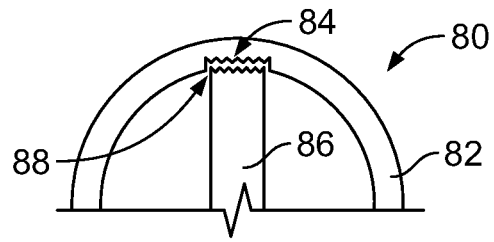
FIG. 7B is a cross-sectional view of a portion of a catheter substrate and a septum in another variation of the embodiment of FIG. 6.

In one manufacturing variation, insertion of the preformed septum 64, which is sized to fit snugly within the lumen of the reinforced substrate 62, is assisted by applying longitudinal pulling tension to the septum in order to stretch the septum 64 and slightly reduce its height. After insertion of the septum 64 into the lumen of the reinforced substrate 62, the tension is released, causing the septum 64 to resume to its natural height and fit tightly therein. The reinforcing element permits this action without resulting in deformation of the cross-sectional shape of the substrate by acting as a stabilizing force. In another variation, the top and bottom sides of the septum are curved or otherwise contoured to match the lumen inside diameter. In yet another variation, the tubular substrate is formed with septum accommodating features, such as notches or cut-away portions on the inner wall. Examples of potential embodiments of such features are illustrated in FIGS. 7A and 7B. FIG. 7A shows an assembly 70 with a substrate 72 having notched or recessed portion 74 on an inner surface thereof, which is configured for receiving a septum 76 having a cooperating protrusion 78. The same notched or recessed portion 74 can also be fashioned on an opposite side of substrate 72 to receive a like protrusion 78 on the opposite end of the septum 76, although certainly other types of cooperating shapes, rounded portions, etc. are possible and are within the scope of this invention. FIG. 7B shows a different type of cooperating shape for an assembly 80, where substrate 82 has a jagged cut-away portion 84 to mesh with jagged protrusion 88 on septum 86. As with FIG. 7A, the opposite side of the substrate 82 and septum 86 can be similarly shaped, although not required.

Figure 8:
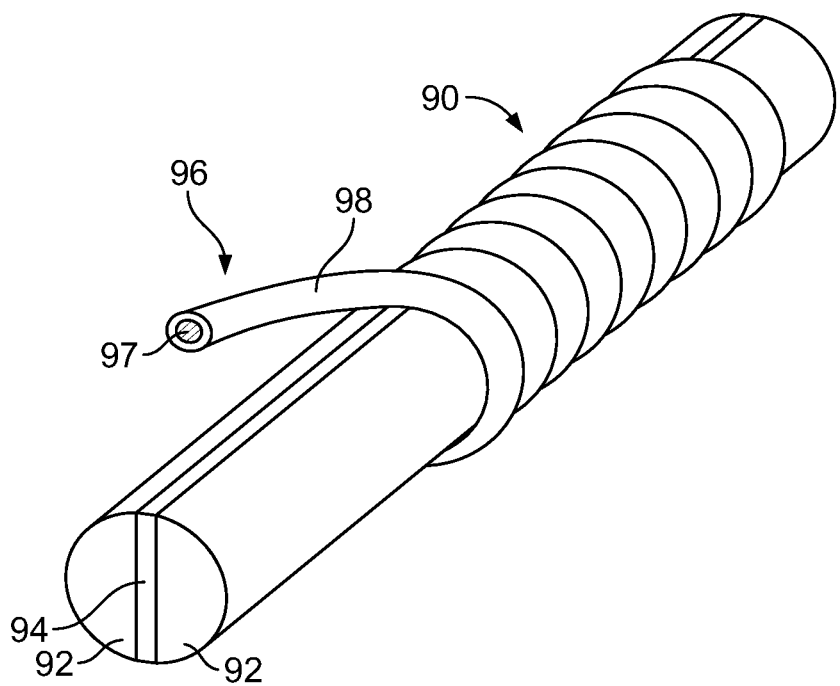
FIG. 8 is a perspective view of another embodiment of an assembly for the manufacture of a multi-lumen catheter according to the present invention.

Another embodiment of the present invention is illustrated in FIG. 8. Assembly 90 is shown with a septum 94 sandwiched between two mandrels 92. In this example, the septum 94 has a rectangular cross-sectional shape and the mandrels have a D-shaped cross-sectional shape; however, it should be appreciated that many shapes and sizes are possible for the septum and mandrels to form any number of catheter lumens of different sizes and configurations, some of which are discussed herein. Wrapped around the combination of mandrels 92 and septum 94 is an elongate member 96, which comprises a reinforcing element 97 with a coating 98, the coating being a polymer, such as polyurethane. The member 96 as shown is cylindrical, having a circular cross-sectional shape, although numerous cross-sectional shapes are possible, depending on, for example, the shape and size of the reinforcing element 97. The member 96 can be wrapped around the mandrels 92 and septum 94 in many different patterns. In the example shown in FIG. 8, the member 96 is wrapped in a helical fashion so that adjacent windings of the member 96 are in contact with one another. The length that the member 96 extends over the mandrels 92 and septum 94 defines the length of the catheter being formed as the member 96, in this example, forms the catheter body. However, in another example, a catheter body substrate is positioned around the mandrels 92 and septum 94 prior to the member 96 being wrapped therearound and thus, the catheter body length in that case is defined by the catheter body substrate. The assembly is then heated (e.g., using shrink tubing) to melt the component parts together, after which the mandrels are removed from the now formed catheter for tipping procedures as necessary.

Figure 9A:
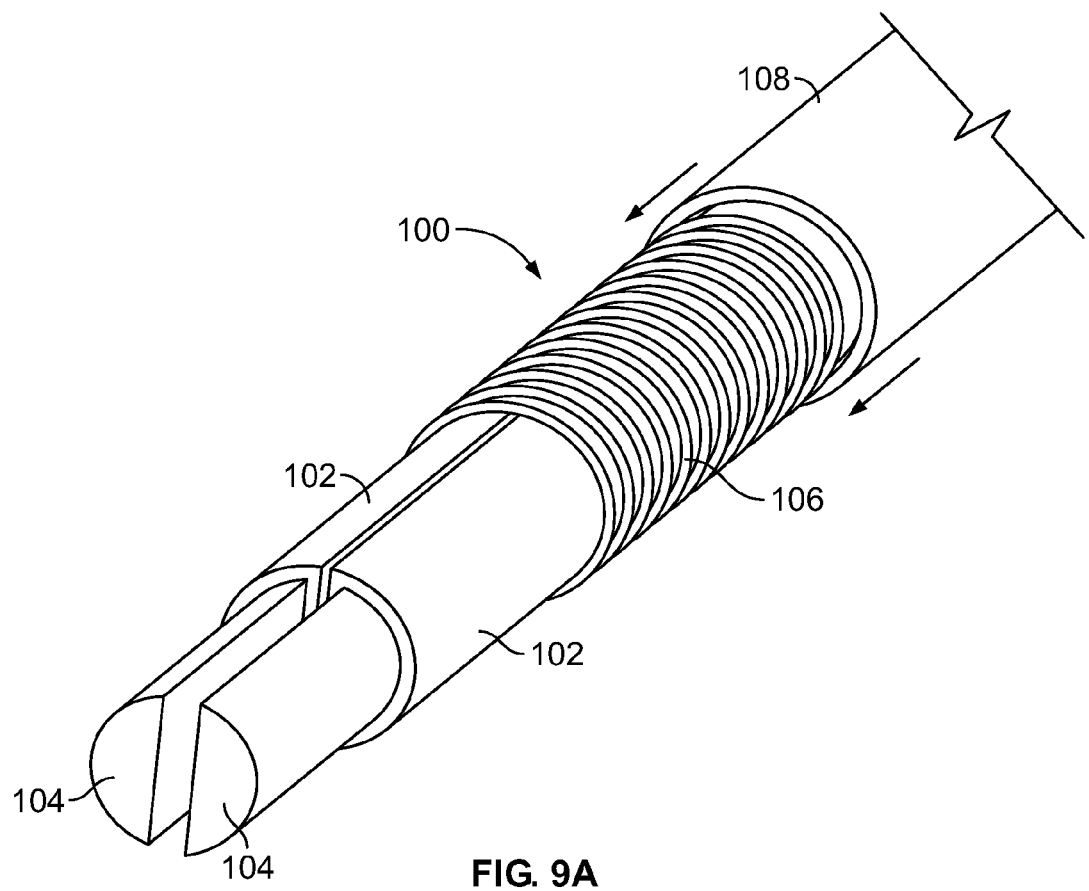
FIG. 9A is a perspective view of another embodiment of an assembly for the manufacture of a multi-lumen catheter according to the present invention.
Figure 9B:
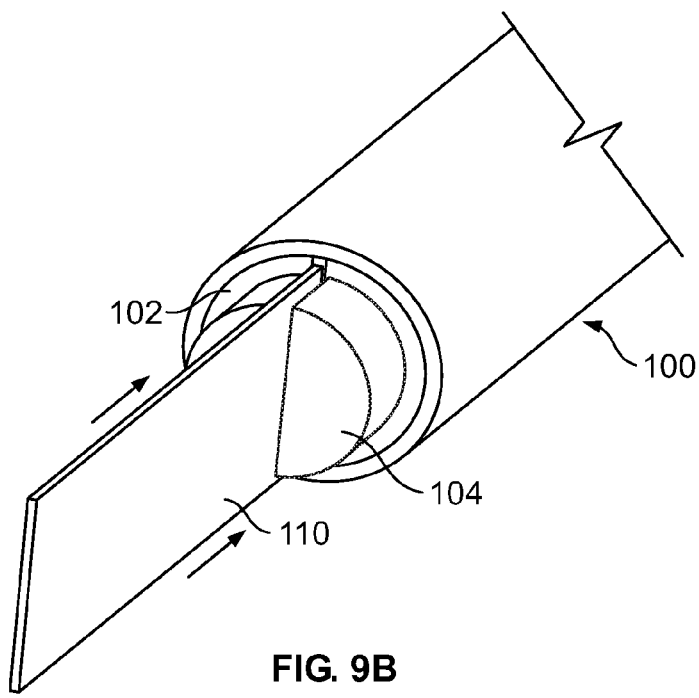
FIG. 9B is an end view of the embodiment of FIG. 9A, showing an additional component in the manufacture of the multi-lumen catheter.

In another embodiment of the present invention, illustrated in FIGS. 9A and 9B as assembly 100, two D-shaped mandrels 104 are inserted through two D-shaped lumen substrates 102, which may have relatively thin walls, and the substrates are brought together to form a circle in cross-section. The D-shaped mandrels 104, in one variation, are slightly bowed on the side that contacts the flat portion of the D-shaped substrates 102 to provide a final catheter with a septum that is slightly thicker at the top and bottom thereof. Such a catheter is adapted for high negative pressures without leading to lumen deformation and collapse. The flat portion of the D-shaped substrates 102 may have a thicker wall than that of the round portion to also provide resistance to lumen deformation and collapse. While the substrates 102 are held together, for example, by a fixture apparatus that holds the mandrels 104 at a fixed distance from one another to avoid relative movement and to rotate the mandrels, a reinforcing element 106 is positioned over a predetermined length of the substrates 102 to form a reinforcing region. The reinforcing element 106 in this example terminates at a point proximal the distal ends of the substrates 102 (e.g., between approximately 8-10 cm from the distal ends of the substrates 102).

The assembly to this point, in one variation, is heated to slightly embed or otherwise fix the reinforcing element 106 in place to prevent movement thereof during further processing steps. A sleeve 108 is then positioned over the entire assembly and, as shown in FIG. 9B, a shim 110 is positioned between the substrates 102 a short distance (e.g., 7-8 cm) equal to that desired for the length of the separate distal tips of a split-tip catheter to be formed in order to prevent bonding of the adjacent walls of the substrates 102 along that length (of course, in the case of the formation of a different type of multi-lumen catheter, the shim may not be necessary at this stage). In one variation, in addition to sleeve 108, a distal sleeve is placed over the region distal the reinforcing region prior to heating in order to provide a substantially uniform outer diameter over the entire length of the catheter. In another variation, a proximal sleeve is placed over the reinforcing region, while a distal sleeve of greater thickness is placed over the region distal the reinforcing region to provide a catheter with a substantially uniform outer diameter. Such use of two separate sleeves of different thicknesses is also contemplated with respect to each embodiment and variation described herein.

After the sleeve or sleeves have been disposed around the reinforcing element 106 and substrates 102, shrink tubing is positioned thereover and the entire assembly 100 is heated to melt the component parts together. The heating step may comprise the use of a "pre-shrink" process in which hot air is blown over the assembly from one end to the other while the assembly is rotated, for example, through the use of the fixture apparatus described above. This process will eliminate any air that may exist in the space between the substrates 102. Following heating, the shrink tubing is removed from the assembly 100 and the sleeve portion that surrounds the shim 110, which is kept in place, is slit along the shim 110 to produce two distal tip sections. The shim 110 is then removed from the assembly 100. In one variation, the shim 110 has sharp edges to slit the sleeve or sleeves. The shim 110 is made of a material with sufficient tensile strength to maintain its profile during the heating process and with sufficient smoothness to enable the removal thereof following the heating process. Examples of potential materials for the shim 110 include stainless steel and PTFE.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A method of making a multi-lumen catheter, comprising:
    providing an assembly comprising:
        a proximal catheter body substrate comprising an outer wall and a septum, the outer wall and the septum defining first and second lumens, the septum comprising a proximal region and a distal region;
        a first distal catheter body substrate comprising a third lumen shaped substantially similar to the first lumen;
        a second distal catheter body substrate comprising a fourth lumen shaped substantially similar to the second lumen;
        a first mandrel and a second mandrel inserted respectively through the first lumen and the second lumen, and into at least a portion of the third lumen and fourth lumen, the first distal catheter body substrate and second distal catheter body substrate placed in abutting relationship with the proximal catheter body substrate;
        a reinforcing element positioned over the proximal catheter body substrate and at least a proximal region of the first and second distal catheter body substrates;
        a sleeve positioned over the reinforcing element;
        shrink tubing positioned over the sleeve;
    heating the assembly; and
    removing the shrink tubing.

2. The method according to claim 1, wherein the first, second, third, and fourth lumens each have a D-shaped configuration.

3. The method according to claim 1, wherein the first distal catheter body substrate has a length different from the second distal catheter body substrate, wherein the first and second mandrels are inserted respectively through the first and second distal catheter body substrates.

4. The method according to claim 1, further comprising the step of forming a tip on at least one of the first and second distal catheter body substrates following the removing step.

5. The method according to claim 1, further comprising the step of forming a tip on both of the first and second distal catheter body substrates following the removing step.

6. The method according to claim 5, wherein the forming includes using radio-frequency energy to form rounded ends on each of the first and second distal catheter body substrates.

7. The method according to claim 6, further comprising creating one or more side holes in the first and second distal catheter body substrates.

8. The method according to claim 1, further comprising attaching a connector system to a proximal end of the proximal catheter body substrate.

9. The method according to claim 1, further comprising the step of splitting the first distal catheter body substrate from the second distal catheter body substrate from a distal end to a predetermined dividing point, the dividing point being distal of the septum proximal region.

10. The method according to claim 1, wherein the shrink tubing comprises an FEP material, the heating step comprising heating a convection oven to a temperature between approximately 300° C. and 360° C., and inserting the assembly into the oven for a period of time between approximately 1 minute and 5 minutes.

* * * * *